(12) United States Patent
Termanini

(10) Patent No.: US 9,427,321 B2
(45) Date of Patent: Aug. 30, 2016

(54) INTERLOCKING ACETABULAR FIXATION SCREWS AND THEIR COMBINATION WITH A REVERSE HIP ACETABULAR CUP

(75) Inventor: Zafer Termanini, Cedar Grove, NJ (US)

(73) Assignee: HIP INNOVATION TECHNOLOGY, LLC, Plantation, FL (US)

( * ) Notice: Subject to any disclaimer, the term of this patent is extended or adjusted under 35 U.S.C. 154(b) by 0 days.

(21) Appl. No.: 14/237,599

(22) PCT Filed: Jul. 20, 2012

(86) PCT No.: PCT/US2012/047518
§ 371 (c)(1),
(2), (4) Date: May 20, 2014

(87) PCT Pub. No.: WO2013/025308
PCT Pub. Date: Feb. 21, 2013

(65) Prior Publication Data
US 2014/0336778 A1     Nov. 13, 2014

Related U.S. Application Data

(60) Provisional application No. 61/574,984, filed on Aug. 13, 2011.

(51) Int. Cl.
*A61F 2/34* (2006.01)
*A61B 17/80* (2006.01)
(Continued)

(52) U.S. Cl.
CPC .............. *A61F 2/34* (2013.01); *A61B 17/8057* (2013.01); *A61B 17/8605* (2013.01); *A61F 2002/30332* (2013.01); *A61F 2002/3401* (2013.01);
(Continued)

(58) Field of Classification Search
CPC ................. A61F 2/34; A61F 2002/34; A61F 2002/3401; A61F 2002/3412; A61F 2002/3432; A61F 2/32; A61F 2002/3414
USPC ........................................... 623/22.21–22.39
See application file for complete search history.

(56) References Cited

U.S. PATENT DOCUMENTS

| 3,916,451 A | 11/1975 | Buechel et al. |
| 4,693,723 A | 9/1987 | Gabard |
| 4,792,337 A * | 12/1988 | Müller ....................... 623/22.36 |

(Continued)

FOREIGN PATENT DOCUMENTS

| FR | 2545352 A1 | 11/1984 |
| WO | 2011005191 A1 | 1/2011 |
| WO | 2011112353 A1 | 9/2011 |

OTHER PUBLICATIONS

International Search report for corresponding application PCT/US12/47518 dated Nov. 16, 2012.

(Continued)

*Primary Examiner* — Alvin Stewart
(74) *Attorney, Agent, or Firm* — Norris McLaughlin & Marcus PA

(57) ABSTRACT

Interlocking acetabular fixation screws having a threaded shaft for threading into cancellous bone and a tapered threaded head for threading into tapered threaded screw holes in a reverse hip acetabular cup. The reverse hip acetabular cup has a central stem and the threaded screw holes are drilled at an angle that allows drilling of the bone of the acetabular cavity, placement of the screws and tightening of the screws without touching the central stem and without interference from the central stem.

12 Claims, 4 Drawing Sheets

(51) Int. Cl.
  *A61F 2/30* (2006.01)
  *A61B 17/86* (2006.01)

(52) U.S. Cl.
  CPC  *A61F2002/3446* (2013.01); *A61F 2002/3483* (2013.01)

(56) References Cited

U.S. PATENT DOCUMENTS

| | | | |
|---|---|---|---|
| 4,813,961 A * | 3/1989 | Sostegni | A61F 2/34 623/22.14 |
| 4,936,861 A * | 6/1990 | Muller et al. | 623/22.24 |
| 5,108,446 A * | 4/1992 | Wagner et al. | 623/22.28 |
| 5,108,447 A * | 4/1992 | Zeiler et al. | 623/22.14 |
| 5,360,448 A | 11/1994 | Thramann | |
| 5,549,695 A * | 8/1996 | Spotorno | A61F 2/34 623/22.23 |
| 5,549,696 A * | 8/1996 | Willi | A61F 2/34 623/22.28 |
| 6,527,809 B1 * | 3/2003 | Doursounian et al. | 623/22.28 |
| 6,790,234 B1 * | 9/2004 | Frankle | 623/19.12 |
| 7,169,185 B2 * | 1/2007 | Sidebotham | 623/22.21 |
| 7,267,693 B1 * | 9/2007 | Mandell et al. | 623/22.28 |
| 7,527,631 B2 | 5/2009 | Maroney et al. | |
| 8,123,815 B2 * | 2/2012 | Meridew et al. | 623/22.29 |
| 8,211,184 B2 * | 7/2012 | Ries et al. | 623/22.21 |
| 8,308,812 B2 * | 11/2012 | Kellar | A61F 2/30767 623/18.11 |
| 8,313,531 B2 * | 11/2012 | Termanini | 623/22.15 |
| 8,540,779 B2 * | 9/2013 | Termanini | 623/22.15 |
| 8,556,984 B2 * | 10/2013 | Calamel | 623/22.13 |
| 8,574,306 B2 * | 11/2013 | Ries et al. | 623/22.21 |
| 8,840,676 B2 * | 9/2014 | Belew et al. | 623/22.15 |
| 8,845,743 B2 * | 9/2014 | Termanini | 623/19.13 |
| 8,992,627 B2 * | 3/2015 | Termanini | 623/22.15 |
| 2003/0153982 A1 * | 8/2003 | Pria | 623/22.24 |
| 2004/0220673 A1 * | 11/2004 | Pria | 623/19.12 |
| 2005/0010303 A1 * | 1/2005 | Nogier | A61F 2/34 623/22.26 |
| 2005/0165490 A1 * | 7/2005 | Tornier | 623/19.13 |
| 2006/0058887 A1 * | 3/2006 | DeSmet et al. | 623/22.36 |
| 2006/0276905 A1 * | 12/2006 | Calamel | 623/22.28 |
| 2007/0142921 A1 * | 6/2007 | Lewis et al. | 623/22.36 |
| 2008/0255672 A1 * | 10/2008 | Gil | 623/22.28 |
| 2009/0088864 A1 * | 4/2009 | Lewis et al. | 623/22.21 |
| 2009/0088865 A1 * | 4/2009 | Brehm | 623/22.21 |
| 2009/0192621 A1 | 7/2009 | Winslow et al. | |
| 2009/0210067 A1 * | 8/2009 | Meridew | 623/22.24 |
| 2010/0114326 A1 | 5/2010 | Winslow et al. | |
| 2010/0256771 A1 * | 10/2010 | Roberts et al. | 623/22.36 |
| 2010/0268348 A1 * | 10/2010 | Ries et al. | 623/22.21 |
| 2011/0054628 A1 * | 3/2011 | Banks et al. | 623/22.19 |
| 2011/0118846 A1 | 5/2011 | Katrana et al. | |
| 2012/0271425 A1 | 10/2012 | Maurer | |
| 2013/0066437 A1 * | 3/2013 | Weeden | 623/22.36 |
| 2015/0127113 A1 * | 5/2015 | Termanini | 623/22.12 |

OTHER PUBLICATIONS

Chinese Office Action for corresponding application CN 201280039481.6 dated May 6, 2015.
Australian Patent Examination Report No. 1 for corresponding application AU 2012295527 dated Sep. 21, 2015.
European Search Report for corresponding application EP 12824127 dated Jul. 4, 2014.

* cited by examiner

INTERLOCKING ACETABULAR FIXATION SCREWS AND THEIR COMBINATION WITH A REVERSE HIP ACETABULAR CUP

BACKGROUND OF THE INVENTION

1. Field of the Invention

The present invention relates generally to interlocking acetabular fixation screws and particularly relates to interlocking acetabular fixation screws for providing a solid fixation of an acetabular cup into a prepared acetabular cavity of a pelvis during a total hip arthroplasty. In a further and more specific aspect, the invention has to do with a combination of a new reverse hip acetabular cup having a stem firmly affixed in the concave portion thereof and the interlocking acetabular fixation screws which are used to firmly affix the cup in the acetabular cavity.

2. The Related Art

It can be appreciated that the securing of an acetabular cup with ordinary screws is known in the prior art. For example, acetabular cups are fixed using conventional cancellous screws with flat heads having a recess for insertion and extraction with common screwdrivers.

Other means of fixation include asperities and voids applied over the convex surface of the acetabular cup, which will allow bone ingrowth.

The main problem with conventional cancellous screws is the fact that they have the tendency to become loose by resorption of bone in the immediate proximity of the screws.

Another problem with conventional cancellous screws is the micro motion caused by movement of the acetabular cup under dynamic load, which seems to initiate loosening and subsequently trigger osteolysis that will lead to bone resorption in and loosening of the implant.

Conventional cancellous acetabular screws also lack the rigidity of screw fixation to the cup under dynamic load, leading to micromotion at the point of contact between the acetabular cup and the screws. As a result, the micromotion leads to fretting and pitting. In addition, metallic debris and wear particulates may consequently be generated, causing local granulomas around the implant.

Interlocking bone screws have been used with conventional flat bone plates, and with acetabular cups such as described in published European Patent Application No. EP 1 800 626 A2. However, proper sizing of the screws has not previously been recognized as a factor in the viability of these screws because they have not been used with reverse hip acetabular cups.

Accordingly, existing cancellous bone screws have failed to adequately address the problem of providing a solid acetabular fixation means into a prepared acetabular cavity of a pelvis during a total hip arthroplasty.

In this respect, the interlocking acetabular fixation screws according to the present invention substantially depart from the conventional sizing of screws of the prior art, and in so doing provides an apparatus primarily developed for the purpose of providing a solid acetabular fixation means into the prepared acetabular cavity of the pelvis during a total hip arthroplasty, particularly in respect of securing the reverse hip acetabular cup of the invention.

SUMMARY OF THE INVENTION

In view of the foregoing disadvantages inherent in the known types and sizes of cancellous acetabular screws now present in the prior art, the present invention provides for a new interlocking acetabular fixation screw construction and sizing for providing cancellous screws to be solidly fixed to a reverse hip acetabular cup upon insertion into the prepared acetabular cavity of the pelvis during a total hip arthroplasty. In particular, the interlocking acetabular fixation screws of the present invention are designed for use in combination with a new reverse hip acetabular cup described in Published PCT Application No. WO 2011-112353-A1, dated Sep. 15, 2011, and entitled "Interlocking Reverse Hip and Revision Prosthesis", wherein the use of properly sized screws provides advantages over screws of the prior art. The new reverse hip acetabular cup is illustrated in perspective in FIG. 3 and in section in FIG. 4.

The general purpose of the present invention, which will be described subsequently in greater detail, is to provide a properly sized interlocking acetabular fixation screw and its combination with the new reverse hip acetabular cup.

To attain this, the present invention generally comprises specially designed interlocking cancellous screws that will be firmly locked into threaded holes in the acetabular cup. The number of the holes normally varies between three and seven and a surgeon may choose to use one or more than one screw to affix the cup to the acetabulum. The interlocking acetabular fixation screws are specifically designed for insertion into threaded screw holes or openings in the acetabular cup of the new reverse hip prosthesis described in the published PCT application referenced above. Said screws have a coarse thread spread over the length of the shank of the screw from the distal end of the screw to the head in order to provide optimal screw fixation in the cancellous bone of the pelvis. The screw head at the proximal end of the screw is tapered and has a fine locking threaded portion. The screw head preferably has a 12 degree taper and the taper angle can vary from 10 degrees to 15 degrees. The head tapers outwardly from the cancellous threads to the proximal end of the screw so that the proximal end of the head has a larger diameter than the end near the cancellous threads. Furthermore, the head at the proximal end of the interlocking acetabular fixation screw provides a hexagonal recess for insertion with a hexagonal screwdriver.

The screw holes in the acetabular cup are also threaded in a tapered fashion to mate with the fine threads of the head of the interlocking acetabular fixation screw. The screw holes of the acetabular cup are also drilled at a specific angle of inclination in order to avoid interference of the drilling instruments, the screws and the screw driver with the central stem of the reverse hip acetabular cup. This feature of the invention also facilitates drilling of the bone and insertion and tightening of the screws.

There has thus been outlined the more important features of the invention in order that the detailed description thereof may be better understood and in order that the present contribution to the art may be better appreciated.

DETAILED DESCRIPTION OF THE INVENTION

Figure 1:
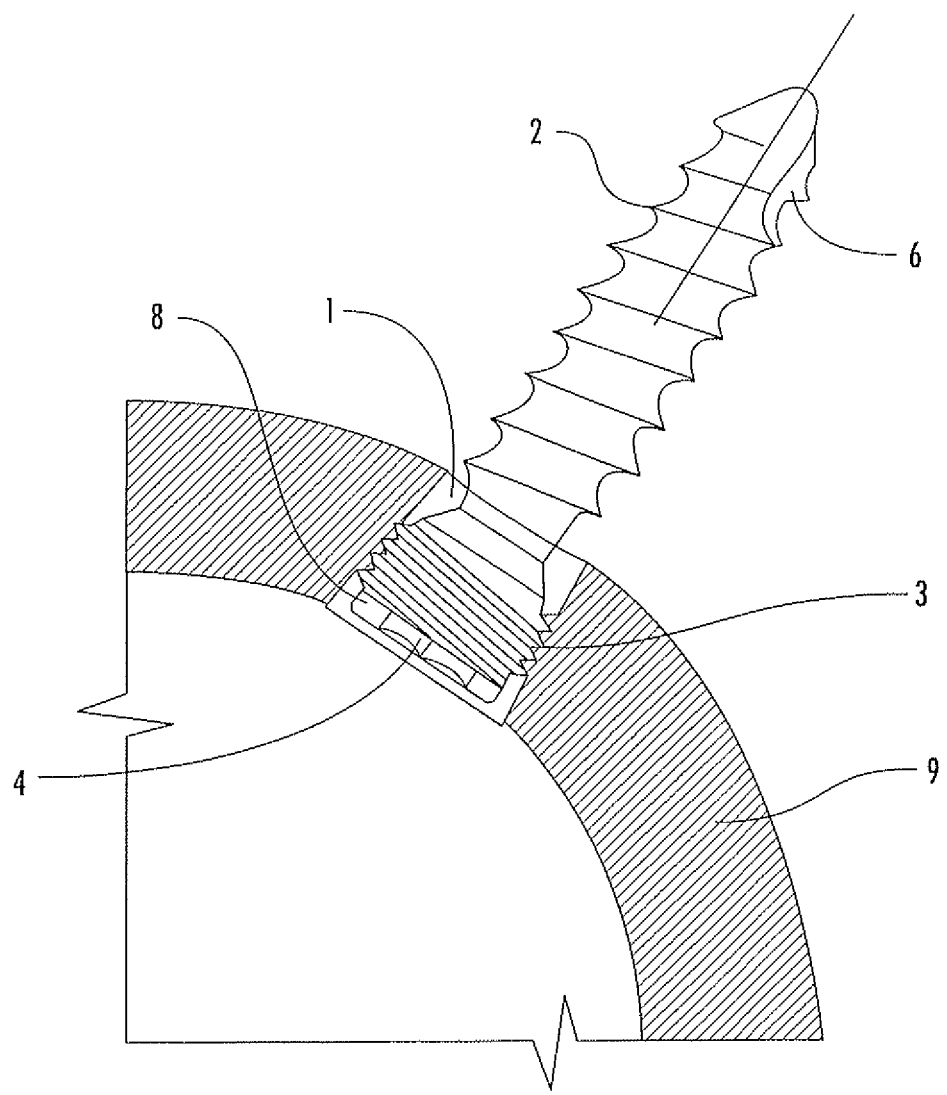
FIG. 1 is a partial section view of the reverse hip acetabular cup with an elevation of an interlocking acetabular fixation screw locked in the cup.

The attached figures illustrate an interlocking acetabular fixation screw 10, which comprises a specially designed and sized interlocking cancellous screw that will be firmly screwed and locked into threaded, tapered acetabular screw holes or openings 1 in acetabular cup 9. Said screws having a course thread 2 over the length of the screw shank, for optimal screw fixation in the cancellous bone of the pelvis, and a fine locking threaded portion 3 on the screw head. The screw head is preferably cut with a 12 degree taper, but the taper angle can vary from 10 degrees to 15 degrees. The head 8 of the interlocking acetabular fixation screw 10 also provides a hexagonal recess 4 for insertion of a hexagonal screwdriver.

Figure 4:
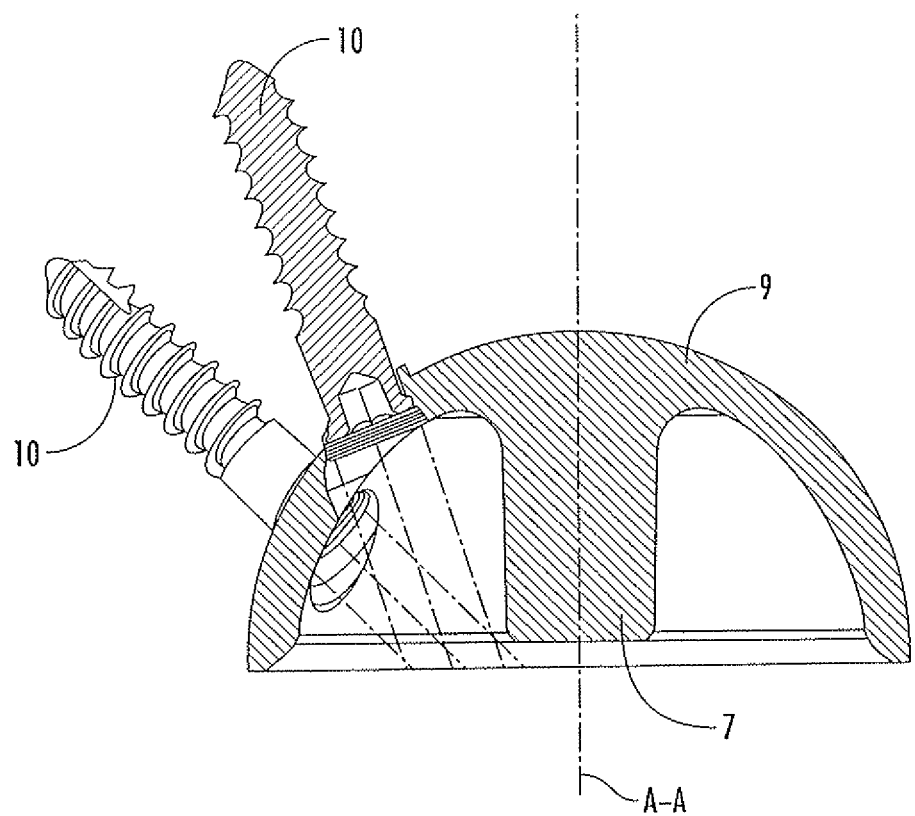
FIG. 4 is a section view of the acetabular cup with two interlocking acetabular fixation screws locked therein, one screw being illustrated in section and the other in perspective elevation.

Referring to FIG. 4, the screw holes or openings in the acetabular cup are drilled at specific angles of inclination in order to avoid interference of the drilling instruments (i.e., the drill guide and/or the drill bit) with the central stem 7 of the acetabular cup 9. As can be seen from FIG. 4, the screw 10 that is illustrated in perspective elevation is at a different angle relative to center line A-A than the screw 10 that is illustrated in section. Moreover, as can be seen from the dotted lines extending in parallel with the central axes of the screws, and away from the heads of the screws, the angles and locations of the screw holes have been selected so that the drill guide, drill bit, screws and screw driver will not touch the central stem 7 and the stem will not interfere with installation of the screws. Thus, when holes are drilled in the acetabular cavity to receive the screws, the stem 7 will not interfere with a drill guide and/or a drill bit. And when a screw 10 is placed in the hole, the stem 7 will not interfere with placement of the screws or with the screw driver used to tighten the screws.

Figure 3:
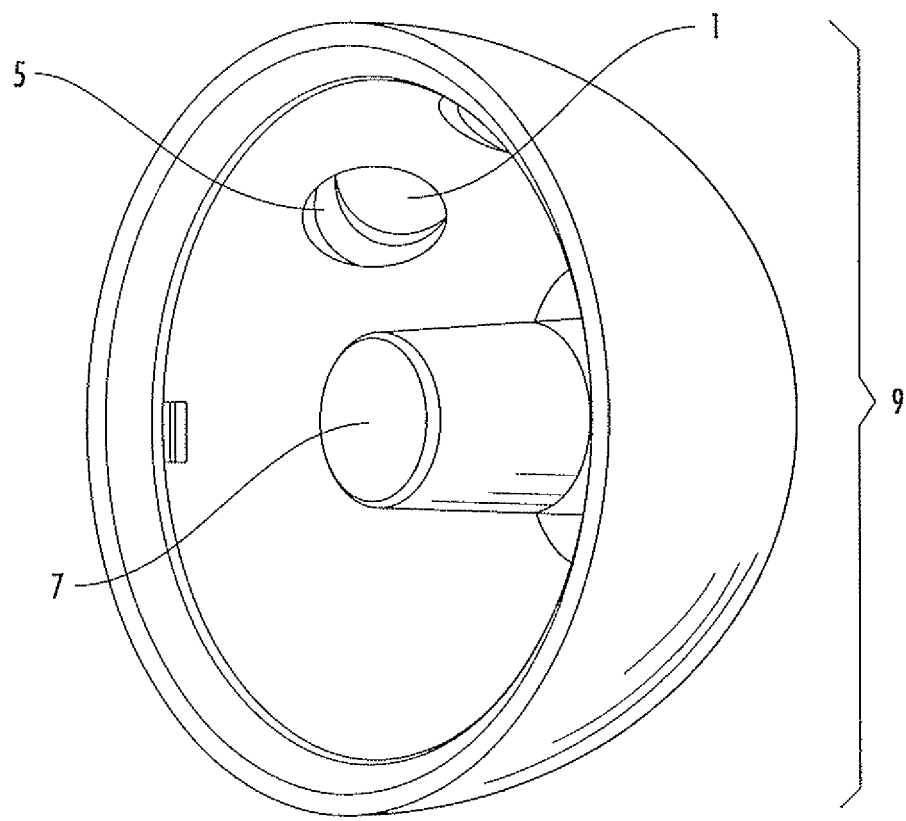
FIG. 3 is a perspective view of the reverse hip acetabular cup with threaded holes.

Referring to FIGS. 3 and 4 and as explained in Published PCT Application No. WO 2011-112353A1 incorporated by reference herein, the reverse hip acetabular cup 9 has a convex outer surface for secure attachment to an acetabular cavity. And the cup 9 has a concave surface having a central stem 7 as a part thereof or firmly affixed therein. The central stem 7 has a central axis A-A (also referred to herein as a first central axis) and the central axis of the stem 7 is the same as the central axis of the cup 9. The cup 9 has at least one internally threaded screw hole having a central axis (also referred to herein as a second central axis) and a circumferential edge. The threaded screw hole is drilled at an angle such that lines extending from the circumferential edge and in parallel with the central axis of the screw hole do not intersect with the central stem. The screw holes 1 are threaded with threads 5 along the tapers thereof to mate with the tapered heads of the interlocking acetabular fixation screws. Furthermore, the tip of the interlocking acetabular fixation screw is self-tapping at 6 for ease of insertion into the bone of the patient.

After the acetabular cavity is prepared by the surgeon, the acetabular cup 9 is impacted in position using an appropriate tool. Using drill guides for angular precision, holes are drilled to the appropriate depth. Interlocking acetabular fixation screws are then inserted until their fine threads 3 mate with the threads 5 of the tapered acetabular screw openings 1 and are tightly locked using a conventional hexagonal screwdriver. In doing so, the interlocking acetabular fixation screws become firmly and lockingly affixed with the acetabular cup 9, as if in one piece, subsequently eliminating any motion between the screw 10 and the cup 9. This is an extremely important factor in eliminating micromotion of the screw thereby reducing osteolysis.

Accordingly, the interlocking acetabular fixation screws firmly secure the acetabular cup and prevent any retrograde migration of the screw head into the acetabular cup, which may cause impingement of the screw head with the moving femoral cup described in the PCT application incorporated by reference herein.

Figure 2:
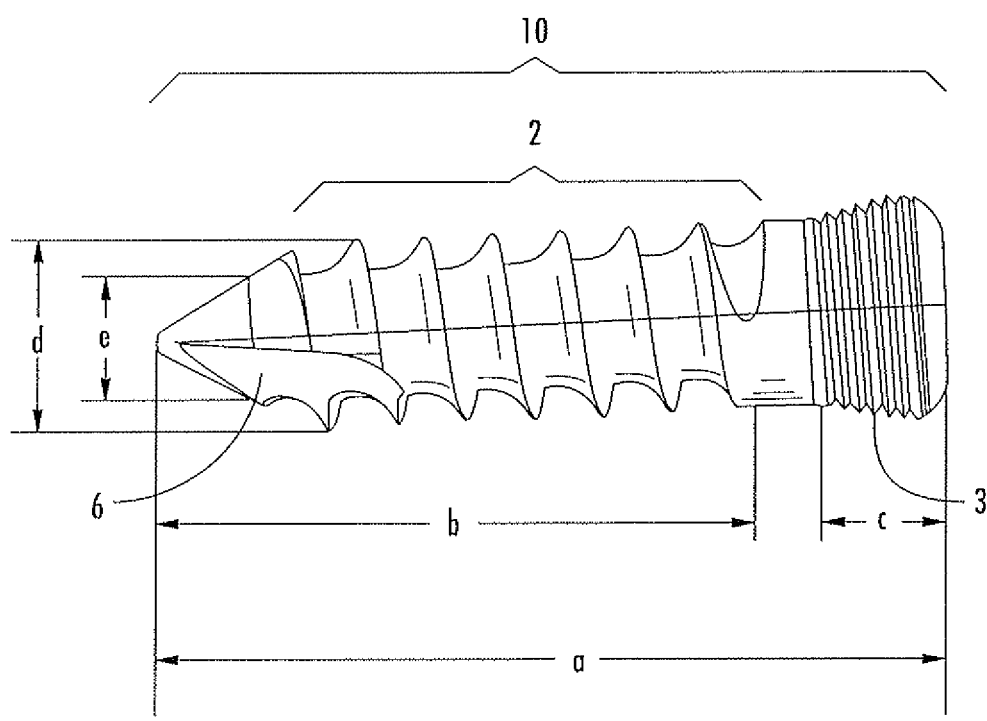
FIG. 2 is an elevation view of the interlocking acetabular fixation screw.

In the preferred embodiment of the invention, the interlocking acetabular fixation screws are sized for specific use with the reverse hip acetabular cup. Referring to FIG. 2, the screws have an overall length a from 21 to 31 millimeters, a cancellous thread length b from 16 to 26 millimeters and a fine head thread length c from 4 to 5 millimeters. The cancellous thread diameter d is from 6 to 7 millimeters and the shank diameter e is from 4 to 5 millimeters.

What is claimed is:

1. A reverse hip acetabular cup having a surface for secure attachment to an acetabular cavity and a concave surface having a central stem extending therefrom,
   the acetabular cup and stem having a common first central axis,
   the acetabular cup comprising at least one threaded screw hole through said acetabular cup, having a second central axis and a circumferential edge on the concave surface
   wherein lines extending from said circumferential edge and in parallel with the second central axis do not intersect with the central stem, and wherein
   i) the central stem is solid and has a male Morse taper, and/or
   ii) the central stem is greater than 7 mm in length, and/or
   iii) the lines extending from the circumferential edge and in parallel with the second central axis do not intersect with the first central axis prior to intersecting an equatorial plane of the acetabular cup.

2. The reverse hip acetabular cup of claim 1 further comprising an interlocking acetabular fixation screw threaded into the at least one threaded screw hole.

3. The reverse hip acetabular cup of claim 2 wherein the threaded screw hole is tapered at an angle from 10 to 15 degrees relative to the second central axis and has a circumference on the concave surface that is larger than the circumference on the convex surface.

4. The reverse hip acetabular cup of claim 3 wherein the interlocking acetabular fixation screw has an externally threaded head, is tapered at the same angle as the threaded screw hole and the threaded head is sized to mate with the threaded screw hole.

5. The reverse hip acetabular cup of claim 2 wherein the screw has a tapered head at an angle from 10 to 15 degrees and an overall length from 21 to 31 millimeters and a shank diameter from 4 to 5 millimeters.

6. The reverse hip acetabular cup of claim 5 wherein the screw has a cancellous thread diameter from 6 to 7 millimeters.

7. The reverse hip acetabular cup of claim 6 wherein the screw has a cancellous thread length from 16 to 26 millimeters.

8. The reverse hip acetabular cup of claim 7 wherein the fine thread head length is from 4 to 5 millimeters.

9. The reverse hip acetabular cup of claim 1, wherein the central stem is solid and has a male Morse taper.

10. The reverse hip acetabular cup of claim 1, the central stem is greater than 7 mm in length.

11. The reverse hip acetabular cup of claim 1, the lines extending from the circumferential edge and in parallel with the second central axis do not intersect with the first central axis prior to intersecting an equatorial plane of the acetabular cup.

12. The reverse hip acetabular cup of claim 1, the central stem is the sole protrusion extending from the acetabular cavity.

* * * * *